United States Patent
Dehghani et al.

(10) Patent No.: US 10,736,942 B2
(45) Date of Patent: Aug. 11, 2020

(54) FORMATION OF BONE

(71) Applicant: ALLERGAN PHARMACEUTICALS INTERNATIONAL LIMITED, Dublin (IE)

(72) Inventors: Fariba Dehghani, Sydney (AU); Ali Fathi, Sydney (AU); Suzanne Marie Mithieux, Sydney (AU); Anthony Steven Weiss, Sydney (AU)

(73) Assignee: Allergan Pharmaceuticals International Limited, Dublin (IE)

( * ) Notice: Subject to any disclaimer, the term of this patent is extended or adjusted under 35 U.S.C. 154(b) by 36 days.

(21) Appl. No.: 15/756,359

(22) PCT Filed: Sep. 1, 2016

(86) PCT No.: PCT/AU2016/050826
§ 371 (c)(1),
(2) Date: Feb. 28, 2018

(87) PCT Pub. No.: WO2017/035595
PCT Pub. Date: Mar. 9, 2017

(65) Prior Publication Data
US 2018/0243381 A1     Aug. 30, 2018

(30) Foreign Application Priority Data

Sep. 1, 2015   (AU) ................. 2015903565

(51) Int. Cl.
*A61K 38/39* (2006.01)
*A61K 9/00* (2006.01)
*A61K 9/06* (2006.01)

(52) U.S. Cl.
CPC ............ *A61K 38/39* (2013.01); *A61K 9/0019* (2013.01); *A61K 9/06* (2013.01)

(58) Field of Classification Search
None
See application file for complete search history.

(56) References Cited

U.S. PATENT DOCUMENTS 4,187,852 A     2/1980   Urry et al.

FOREIGN PATENT DOCUMENTS

| CA | 2596266 | 8/2006 |
|----|---------|--------|
| WO | WO 99/03886 | 1/1999 |
| WO | 2010078620 | 7/2010 |
| WO | WO 2010/102337 | 9/2010 |
| WO | 2012068619 | 5/2012 |
| WO | 2014063194 | 5/2014 |
| WO | 2014089610 | 6/2014 |
| WO | WO 2015/054718 | 4/2015 |

OTHER PUBLICATIONS

Annabi et al. (2013) "Engineered cell-laden human protein-based elastomer" Biomaterials; 34(22):5496-5505.
Hu et al. (2011) "The influence of elasticity and surface roughness on myogenic and osteogenic-differentiation of cells on silk-elastin biomaterials" Biomaterials; 32(34):8979-8989.
Nusselt et al., "Cerament treatment of fracture defects (CERTiFy): protocol for a prospective, multicenter, randomized study investigating the use of Cerament Bone Void Filler in tibial plateau fractures," Trials, Mar. 8, 2014, 11 pages.

*Primary Examiner* — Elizabeth C. Kemmerer
(74) *Attorney, Agent, or Firm* — Nathan S. Smith; Gail H. Griffin; Morgan, Lewis & Bockius LLP

(57) ABSTRACT

Compositions and methods for inducing or promoting repair of a bone fracture.

13 Claims, 11 Drawing Sheets
Specification includes a Sequence Listing.

SEQ ID NO:1

```
Gly Gly Val Pro Gly Ala Ile Pro Gly Gly Val Pro Gly Gly Val Phe
Tyr Pro Gly Ala Gly Leu Gly Ala Leu Gly Gly Gly Ala Leu Gly Pro
Gly Gly Lys Pro Leu Lys Pro Val Pro Gly Gly Leu Ala Gly Ala Gly
Leu Gly Ala Gly Leu Gly Ala Phe Pro Ala Val Thr Phe Pro Gly Ala
Leu Val Pro Gly Gly Val Ala Asp Ala Ala Ala Tyr Lys Ala Ala
Lys Ala Gly Ala Gly Leu Gly Gly Val Pro Gly Val Gly Gly Leu Gly
Val Ser Ala Gly Ala Val Val Pro Gln Pro Gly Ala Gly Val Lys Pro
Gly Lys Val Pro Gly Val Gly Leu Pro Gly Val Tyr Pro Gly Gly Val
Leu Pro Gly Ala Arg Phe Pro Gly Val Gly Val Leu Pro Gly Val Pro
Thr Gly Ala Gly Val Lys Pro Lys Ala Pro Gly Val Gly Gly Ala Phe
Ala Gly Ile Pro Gly Val Gly Pro Phe Gly Gly Pro Gln Pro Gly Val
Pro Leu Gly Tyr Pro Ile Lys Ala Pro Lys Leu Pro Gly Gly Tyr Gly
Leu Pro Tyr Thr Thr Gly Lys Leu Pro Tyr Gly Tyr Gly Pro Gly Gly
Val Ala Gly Ala Ala Gly Lys Ala Gly Tyr Pro Thr Gly Thr Gly Val
Gly Pro Gln Ala Ala Ala Ala Ala Ala Lys Ala Ala Ala Lys Phe
Gly Ala Gly Ala Ala Gly Val Leu Pro Gly Val Gly Gly Ala Gly Val
Pro Gly Val Pro Gly Ala Ile Pro Gly Ile Gly Gly Ile Ala Gly Val
Gly Thr Pro Ala Ala Ala Ala Ala Ala Ala Ala Ala Lys Ala Ala
Lys Tyr Gly Ala Ala Gly Leu Val Pro Gly Gly Pro Gly Phe Gly
Pro Gly Val Val Gly Val Pro Gly Ala Gly Val Pro Gly Val Gly Val
Pro Gly Ala Gly Ile Pro Val Val Pro Gly Ala Gly Ile Pro Gly Ala
Ala Val Pro Gly Val Val Ser Pro Glu Ala Ala Lys Ala Ala Ala
Lys Ala Ala Lys Tyr Gly Ala Arg Pro Gly Val Gly Val Gly Gly Ile
Pro Thr Tyr Gly Val Gly Ala Gly Gly Phe Pro Gly Phe Gly Val Gly
Val Gly Gly Ile Pro Gly Val Ala Gly Val Pro Ser Val Gly Gly Val
Pro Gly Val Gly Gly Val Pro Gly Val Gly Ile Ser Pro Glu Ala Gln
Ala Ala Ala Ala Ala Lys Ala Ala Lys Tyr Gly Val Gly Thr Pro Ala
Ala Ala Ala Ala Lys Ala Ala Lys Ala Ala Gln Phe Gly Leu Val
Pro Gly Val Gly Val Ala Pro Gly Val Gly Val Ala Pro Gly Val Gly
Val Ala Pro Gly Val Gly Leu Ala Pro Gly Val Gly Val Ala Pro Gly
```

Figure 9 (continued)

```
Val Gly Val Ala Pro Gly Val Gly Val Ala Pro Gly Ile Gly Pro Gly
Gly Val Ala Ala Ala Ala Lys Ser Ala Ala Lys Val Ala Ala Lys Ala
Gln Leu Arg Ala Ala Ala Gly Leu Gly Ala Gly Ile Pro Gly Leu Gly
Val Gly Val Gly Val Pro Gly Leu Gly Val Gly Ala Gly Val Pro Gly
Leu Gly Val Gly Ala Gly Val Pro Gly Phe Gly Ala Val Pro Gly Ala
Leu Ala Ala Ala Lys Ala Ala Lys Tyr Gly Ala Ala Val Pro Gly Val
Leu Gly Gly Leu Gly Ala Leu Gly Gly Val Gly Ile Pro Gly Gly Val
Val Gly Ala Gly Pro Ala Ala Ala Ala Ala Ala Ala Lys Ala Ala Ala
Lys Ala Ala Gln Phe Gly Leu Val Gly Ala Ala Gly Leu Gly Gly Leu
Gly Val Gly Gly Leu Gly Val Pro Gly Val Gly Gly Leu Gly Gly Ile
Pro Pro Ala Ala Ala Ala Lys Ala Ala Lys Tyr Gly Ala Ala Gly Leu
Gly Gly Val Leu Gly Gly Ala Gly Gln Phe Pro Leu Gly Gly Val Ala
Ala Arg Pro Gly Phe Gly Leu Ser Pro Ile Phe Pro Gly Gly Ala Cys
Leu Gly Lys Ala Cys Gly Arg Lys Arg Lys
```

FORMATION OF BONE

FIELD OF THE INVENTION

The invention relates to formation of bone, including repair of bone wounds and fractures, and to elastin.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

It is estimated that up to 2.2 million bone grafting procedures are performed annually [1]. As a result of injury or tumour resection, the loss of large quantities of bone tissue can overwhelm the body's natural bone healing capacity, leading to non-union. Together with infection, poor bone healing associated with major bone loss remain key challenges for orthopaedic medicine.

Non-union results in recurrent surgical procedures and long in-hospital stays which is challenging for both patients and surgeons [2, 3]. Two of the key causes that lead to non-union are an insufficiency of biological factors required for repair, and infection of the bone (osteomyelitis) [3, 4].

Insufficient biological factors can result from a large bone defect size, lack of biological growth factors (which can be further depleted by wound debridement) as well as damaged or reduced blood supply. Current treatments to restore osteogenic factors and an appropriate microenvironment include bone grafting [5], bone transport [6, 7], addition of growth factors and tissue engineering approaches. Nevertheless, all of these methods have limitations and there is an ongoing search for more effective agents.

WO2012/068619, WO2014/063194 and WO2014/089610 discuss utilising the structural characteristics of tropoelastin for formation of hydrogels, scaffolds and the like. These structures may then be adapted for use in therapeutic applications by attaching or seeding them with biological factors or cells that are required for therapy at a site or location where the structure is to be placed. Where therapy requires bone formation, WO2012/068619, WO2014/063194 and WO2014/089610 disclose that it is the biological factors (for example bone morphogenic proteins) or cells (osteocytes) attached to the tropoelastin-based structure that provide for the therapy.

There is a need for new approaches to bone formation in therapeutic applications.

SUMMARY OF THE INVENTION

The invention seeks to address one or more of the above mentioned needs or limitations, or to provide an alternative approach to bone formation and in one embodiment provides a use of tropoelastin or compositions including same for inducing or promoting bone formation.

In another embodiment there is provided tropoelastin or compositions including same for use in inducing or promoting bone formation.

In another embodiment there is provided tropoelastin or compositions including same in the manufacture of a medicament for use in inducing or promoting bone formation. The medicament may take the form of a composition, formulation, scaffold, matrix or hydrogel, as described below.

In another embodiment there is provided a method for inducing or promoting bone formation including:
providing an individual requiring bone formation,
providing an amount of tropoelastin effective for inducing or promoting bone formation to the individual, thereby inducing bone formation in the individual.

Typically the tropoelastin is provided to a site or region of bone or bone-related tissue in which bone formation is required.

In other embodiments there is provided a use of tropoelastin or compositions including same for inducing anabolism of bone.

In another embodiment there is provided tropoelastin or compositions including same for use in inducing anabolism of bone.

In another embodiment there is provided tropoelastin or compositions including same in the manufacture of a medicament for use in inducing anabolism of bone. The medicament may take the form of a composition, formulation, scaffold, matrix or hydrogel, as described below.

In another embodiment there is provided a method for inducing anabolism of bone including:
providing an individual requiring induction of bone anabolism,
providing an amount of tropoelastin effective for inducing anabolism of bone to the individual, thereby inducing anabolism of bone in the individual.

Typically the tropoelastin is provided to a site or region of bone or bone-related tissue in which anabolism of bone is required.

In other embodiments there is provided a use of tropoelastin or compositions including same for increasing the volume or density of bone tissue.

In another embodiment there is provided tropoelastin or compositions including same for use in increasing the volume or density of bone tissue.

In another embodiment there is provided tropoelastin or compositions including same in the manufacture of a medicament for use in increasing the volume or density of bone tissue. The medicament may take the form of a composition, formulation, scaffold, matrix or hydrogel, as described below.

In another embodiment there is provided a method for increasing the volume or density of bone tissue including:
providing an individual requiring increased bone tissue volume or density,
providing an amount of tropoelastin effective for increasing the volume or density of bone tissue to the individual,
thereby increasing the volume or density of bone tissue in the individual.

Typically the tropoelastin is provided to a site or region of bone or bone-related tissue in which increased volume or density of bone tissue is required.

The above described methods or uses may be applied to strengthen bone, to repair a bone defect, or to other clinical outcome in which bone formation is necessary.

In the above described methods or uses, the tropoelastin may be provided to the individual or site or region of bone or bone-related tissue in the form of a composition, formulation, scaffold, matrix or hydrogel, as described below.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 9—sequence of the tropoelastin SHELδ26A isoform

DETAILED DESCRIPTION OF THE EMBODIMENTS

Figure 1:
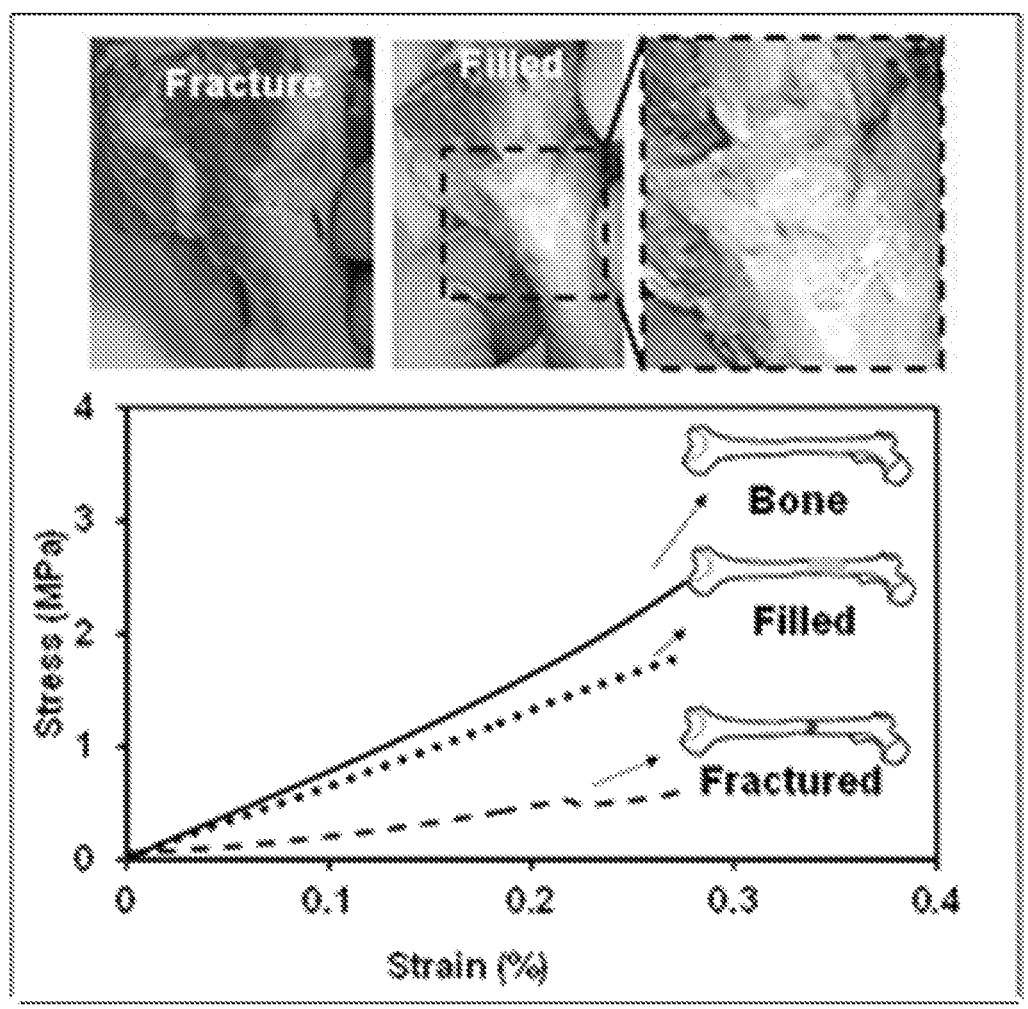
FIG. 1—Biomechanical behaviour of bone before and after injection of tropoelastin hydrogel FIG. 2—The subcutaneous injection site of the tropoelastin hydrogels at different time points.

The inventors provide herein tropoelastin and compositions including same that are suitable for use in promoting or inducing bone production or formation and that advantageously have properties of being adherent to bone, injectable, angiogenic, osteogenic and/or bioabsorbable. According to the invention, tropoelastin is utilised principally to induce the formation or production of bone in clinical applications where bone production or formation is required.

A. Definitions

The term "comprise" and variations of the term, such as "comprising", "comprises" and "comprised", are not intended to exclude further additives, components, integers or steps.

"Bone" generally refers to a mineralized tissue primarily comprising a composite of deposited calcium and phosphate in the form of hydroxyapatite, collagen (primarily Type I collagen) and bone cells such as osteoblasts, osteocytes and osteoclasts, as well as to bone marrow tissue. Bone is a vascularised tissue.

Bone is generally in the form of "compact bone" (or "cortical bone") or "spongy bone" (or "cancellous bone"). From a gross anatomical perspective there are clear differences between compact and spongy bone. Specifically, compact bone has a lamellar structure and generally represents a dense area of bone tissue that does not contain cavities, whereas spongy bone contains numerous interconnecting cavities defined by complex trabeculae. Compact bone is typically harder, stronger and stiffer than cancellous bone. The higher surface area to mass ratio of cancellous bone compared to compact bone means that cancellous bone is less dense than compact bone and is generally softer, weaker and more flexible than compact bone. Cancellous bone is highly vascularised and is typically found at the ends of long bones, proximal to joints and within the interior of vertebrae. Compact bone typically forms a "shell" around cancellous bone and is the primary component of the long bones of the arm and leg and other bones, where its greater strength and rigidity are needed. The primary anatomical and functional unit of compact bone is the osteon and the primary anatomical unit of cancellous bone is the trabecula.

"Long bones" are generally bones in which compact bone is found at the diaphysis, which is the cylindrical part of the bone, whereas the spongy bone is found at the epiphyses, i.e. the bulbous ends of a bone. Examples of long bones include humerus, radius, ulnar, tibia, fibular and femur.

"Short bones" are generally bones where there is usually a core of spongy bone completely surrounded by compact bone. Examples include the bones of the hand.

"Flat bones" generally have 2 layers of compact bone called plates separated by a layer of spongy bone. Examples of flat bones include parietal, frontal, occipital and temporal bones of the skull, the mandible and maxilla.

"Endochondral ossification" generally refers to production of bone within cartilage tissue, as generally occurs in fetal skeletal system development. This bone production generally occurs at a primary ossification centre at the diaphyses, and then at a secondary ossification centre at the epiphyses. Endochondral ossification is generally required for formation of long and short bones.

"Intramembranous ossification" is another important process for development of the fetal skeletal system, although unlike endochondral ossification, intramembranous ossification generally refers to production of bone that does not occur within cartilage. Intramembranous ossification is generally required for formation of flat bones. Intramembranous ossification is also an essential process during the natural healing of bone fractures "Subchondral bone" is generally bone located below cartilage, and therefore generally provides support for a cartilaginous articular surface.

"Bone-related tissue" generally refers to tissue that is either supported by bone (for example articular tissue) or tissue that is connected to bone, for example, a ligament or tendon. Generally, bone-related tissue is cartilaginous.

"Inducing or promoting bone formation" generally refers to an anabolic process the end result of which is bone. Generally this does not involve a catabolic process that leads to re-modelling of bone. However, the bone arising from inducing or promoting bone formation in accordance with the invention may be remodelled with or without clinical intervention. In certain embodiments the induction or promotion of bone formation involves a process that more closely resembles intramembranous ossification.

As described herein and exemplified in the examples, the process generally involves the proliferation and differentiation of osteoblasts and the mineralisation of calcium. The process may or may not require the presence of cartilaginous tissue.

A "bone defect" is generally a structural disruption of bone requiring repair. A defect can assume the configuration of a "void", which is understood to mean a three-dimensional defect such as, for example, a gap, cavity, hole or other substantial disruption in the structural integrity of a bone or joint. A defect can be the result of accident, disease, surgical manipulation, and/or prosthetic failure. The defect may be a void having a volume incapable of endogenous or spontaneous repair. Generally, these are capable of some spontaneous repair, albeit biomechanically inferior. Other defects susceptible to repair include, but are not limited to, non-union fractures; bone cavities; tumor resection; fresh fractures (distracted or undistracted); cranial/facial abnormalities; periodontal defects and irregularities; spinal fusions; as well as those defects resulting from diseases such as cancer, arthritis, including osteoarthritis, and other bone degenerative disorders such as osteochondritis dessicans.

"Repair" generally refers to new bone formation which is sufficient to at least partially fill a void or structural discontinuity at a defect. Repair does not, however, mean, or otherwise necessitate, a process of complete healing or a treatment which is 100% effective at restoring a defect to its pre-defect physiological/structural/mechanical state.

When a bone is fractured, the damaged blood vessels produce a localized haemorrhage with formation of a blood clot. Destruction of bone matrix and death of bone cells adjoining the fracture may also occur. During repair, the blood clot, the remaining cells, and the damaged bone matrix may be removed by macrophages. The periosteum (the connective tissue membrane covering the bone) and the endosteum (the thin vascular membrane of connective tissue that lines the surface of the bony tissue that forms the medullary cavity of long bones) around the fracture respond with intense proliferation of osteoprogenitor cells, which form a cellular tissue surrounding the fracture and penetrating between the extremities of the fractured bone. Immature bone is then formed by endochondral ossification of small cartilage fragments that appear in the connective tissue of the fracture. Depending on the nature of the bone injury or fracture, the periosteum may be largely intact following the injury (i.e., still connected to the bone). In this scenario, the endosteum may or may not be damaged as a result of the injury and therefore may or may not contribute to repair. In other circumstances, there may be significant destruction to the periosteum (for example, a significant trauma or a surgical procedure), wherein the periosteum is no longer in contact with the bone surface. Under these circumstances, the contribution of the periosteum to bone repair may not be possible without alternative intervention.

Bone is also formed by means of intramembranous ossification. Repair progresses in such a way that irregularly formed trabeculae of immature bone temporarily unite the extremities of the fractured bone forming a "bone callus". Normal stress imposed on the bone during repair and during return to activity serves to remodel the bone callus, influencing its structure, and the primary bone tissue of the callus is therefore gradually reabsorbed and replaced by lamellar bone, resulting in restoration of the original bone structure and function.

"Tropoelastin" is generally a monomeric protein from which elastin is formed. Tropoelastin is generally not cross linked, covalently or otherwise. Tropoelastin may reversibly coacervate. Tropoelastin may be synthetic, for example it may be derived from recombinant expression or other synthesis, or it may be obtained from a natural source such as porcine aorta. As generally known in the art, tropoelastin may exist in the form of a variety of fragments.

B. Bone Formation

It will be understood that the invention applies to the induction or promotion of bone formation. In one embodiment, there is provided a method for inducing or promoting bone formation. The method includes the following steps:
provided an individual requiring bone formation,
providing tropoelastin to the individual to induce or promote the formation of bone in the individual,
thereby inducing bone formation in the individual.

The individual may require bone formation for the purpose of remedying or repairing a bone defect. The bone defect may be a fracture, such as a non-union fracture or a fresh fracture (distracted or undistracted). The bone defect may result in minor damage to the periosteum. In this circumstance, there may be no damage to the endosteum. Alternatively, the bone defect may include damage to both the periosteum and endosteum. The bone defect may be a fracture or microfracture made during a controlled surgical procedure or as a result of a trauma. Thus in one embodiment there is provided a method for repairing a bone fracture including the following steps:
providing an individual requiring repair of bone fracture,
providing tropoelastin to the individual to repair the bone fracture in the individual,
thereby repairing a bone fracture in the individual.

In another embodiment the individual requires bone formation for the filling of a void in bone tissue. The void may generally be a three dimension defect such as a gap, cavity or hole arising from disease, surgical manipulation and/or prosthetic failure. The void may have a volume incapable of endogenous or spontaneous repair. For example the void may be twice the diameter of the subject bone. Thus in another embodiment there is provided a method for filling a void in bone including the following steps:
providing an individual having a void in a bone,
providing tropoelastin to the individual to fill the void in the bone of the individual,
thereby filling the void in the bone.

Typically the tropoelastin is provided to a site or region of bone or bone-related tissue in which bone formation is required. In this embodiment, the tropoelastin is provided by local administration of tropoelastin to the site or region of bone or bone related tissue. Local administration generally requires direct contact of the site or region of bone or bone-related tissue with the tropoelastin.

The tropoelastin may be provided for direct contact with a site or region of bone or bone-related tissue by applying tropoelastin in the form of a composition, formulation, scaffold or matrix described below to the site or region of bone or bone related tissue. In more detail, and as described further herein, in some embodiments at least some tropoelastin contained in the formulation is not cross linked, bonded or otherwise covalently attached to other components of the composition or formulation, for example, not attached to a scaffold or matrix. This enables at least some, if not all tropoelastin provided in these formulations to be released from the composition to tissue at the site of bone or bone related tissue that requires repair, thereby enabling the tropoelastin to stimulate the tissue elements at that site for bone production. The direct contact of the tropoelastin of these formulations with the site of bone or bone-related tissue requiring bone formation or production enables tropoelastin to induce the formation or production of bone at the site.

The tropoelastin may be applied to bone only, or to bone and bone-related tissue. For example, in the context of a surgical procedure the tropoelastin may be applied to the bone only. Examples, of surgical procedures in which tropoelastin may be subsequently utilised to promote an osteoinductive or osteoconductive environment include: cranial, jaw and dental repair, knee arthroscopy and meniscectomy; shoulder arthroscopy and decompression; carpal tunnel release; knee arthroscopy and chondroplasty; knee arthroscopy and anterior cruciate ligament reconstruction; total knee replacement; repair of femoral neck fracture; repair of trochanteric fracture; knee arthroscopy repair of both menisci; total hip replacement; shoulder arthroscopy/distal clavicle excision; repair of rotator cuff tendon; repair fracture of radius (bone)/ulna; laminectomy; repair of ankle fracture (bimalleolar type); shoulder arthroscopy and debridement; lumbar spinal fusion; repair fracture of the distal part of radius; lower back intervertebral disc surgery; incise finger tendon sheath; repair of ankle fracture (fibula); repair of femoral shaft fracture; repair of trochanteric fracture. Other examples of surgical procedures which may require the subsequent induction of bone repair include cardiothoracic surgeries, which require cutting of the sternum (a median sternotomy) to gain access to the thoracic contents.

The tropoelastin may be applied to periosteum only, or endosteum only, or to both periosteum and endosteum. For example, where bone microfracture or microdrilling has occurred, the tropoelastin will typically be applied to the periosteum only. Where a full fracture of the bone has occurred through trauma (such as a bilateral fracture of the diaphysis of a long bone), the tropoelastin will typically be applied to both the periosteum and the endosteum.

The tropoelastin may be applied to compact bone only, or spongy bone only, or to both spongy and compact bone. For example, in the context of a surface fracture of the bone, in which only the compact bone is damaged, the tropoelastin will be applied to the compact bone only. Where both compact and spongy bone are damaged and an osteoinductive and osteoconductive environment is required, the tropoelastin may be applied to both the spongy and compact bone. In microdrilling applications into an articular surface supported by spongy bone, the tropoelastin may be applied to spongy bone only.

Where the objective is to repair a defect in the form of a fracture, the tropoelastin may be applied by direct contact to the bone at the site of the fracture, including to one or more of the periosteum, endosteum, or callus. In this embodiment the tropoelastin may be provided on or below the periosteum.

Where the objective is to fill a void in bone, for example a gap, cavity, hole or other, the tropoelastin may be provided on or below the periosteum.

In one embodiment, the method is for formation of intramembranous bone, or formation of spongy bone, or both.

As described herein, the invention further provides for inducing the anabolism of bone. Specifically, as exemplified herein, the inventors have found improvements in bone formation seen with tropoelastin treatment result from a mechanism primarily involving bone anabolism. The finding is significant as few other biological factors have been found to have this function. Bone anabolism is particularly required where there is a clinical need to increase bone density, or to increase bone volume. Thus in one embodiment there is provided a method for inducing anabolism of bone including:
 providing an individual requiring induction of bone anabolism,
 providing an amount of tropoelastin effective for inducing anabolism of bone to the individual,
 thereby inducing anabolism of bone in the individual.

In one embodiment, the individual may require treatment to increase bone density. For example, the individual may have a form of osteoporosis.

In another embodiment, the invention provides for increase in volume of bone tissue. In this embodiment, the outcome of anabolism may be increases in any one or more dimensions of bone. This treatment may be particularly relevant where the intention is to improve the volume of an improperly formed bone. Thus there is provided a method for increasing the volume of bone tissue including:
 providing an individual requiring increased bone tissue volume,
 providing an amount of tropoelastin effective for increasing the volume of bone tissue to the individual,
 thereby increasing the volume of bone tissue in the individual.

Where the objective is to repair a defect in the form of low bone density (such as due to osteoporosis), the tropoelastin may be applied by direct contact to the bone including to one or more of the periosteum, endosteum, or callus. In this embodiment the tropoelastin may be provided on or below the periosteum. In a further embodiment, the tropoelastin may be provided to an endosteum region by micro-drilling of cortical bone.

In the above described embodiments tropoelastin may be applied to subchondral bone, i.e. adjacent bone related tissue, or it may be contacted with bone to permit bone formation in the absence of cartilaginous tissue.

The tropoelastin may be applied to a long bone, short bone or flat bone.

In one embodiment, the method may involve the administration of a further compound for influencing bone production. The compound may be one that is anabolic, in the sense that it is involved in new bone production, or catabolic, in the sense of causing bone re-sorption.

For the treatment of fracture, a composition containing from 0.1 mg/ml to 100 mg/ml of tropoelastin, preferably from 1.0 to 75 mg/ml tropoelastin, more preferably from 2.0 to 50 mg/ml tropoelastin may be prepared in sterile water. The composition is preferably prepared as an injectable composition.

The composition is generally injected into the site of the injury. In one embodiment it is preferable to inject directly into the soft tissue adjacent to the fracture. In another embodiment it could be administered by intra osseous injection. This could be performed in saline, injectable ceramic, or other high viscosity carrier.

Preferably the injection permits tropoelastin to be delivered to at least one, and more preferably, one or more opposing surfaces formed from the fracture. Generally it is preferable to achieve an even application of the tropoelastin across all of the relevant opposing surfaces.

Clinically the preferred method would be to apply via surgical means only a single time with or without other agents. Follow up doses by percutaneous injection or topical application could be applied. Follow up dosing could be a preferred method for preventing or treating bone infection. Alternatively an implant could be used that allows for sustained in vivo dosing using tropoelastin. One example of this could be the use of sucrose acetate isobutyrate.

Injections, including follow up injections, may be made more than once a week, and typically twice a week i.e. 'biweekly'. The injections may be administered for a period of about three to four weeks.

In one embodiment, a bolus of tropoelastin may be delivered by injection of tropoelastin more or less immediately after fracture In another embodiment, the tropoelastin may be applied in the form of a hydrogel, putty, paste, sponge or scaffold. A cellular collagen sponges or other bioresorbable carriers may be preferred. This could include a carboxymethylcelulose, a collagen putty or a high viscosity carrier medium such as sucrose acetate isobuyrate. It could also be delivered via polymer scaffolds, including PLLA, PLGA, PGA, PCL. It could also be applied topically or by direct injection.

In one embodiment, tropoelastin could be applied into the fracture at the time of fracture or prior to casting for closed fractures. For open fractures it could be introduced to the fracture gap after debridement of the wound area. For wounds where infection is suspected it could be injected adjacent to the healing fracture or into the intra osseous space as mentioned above.

The outcome of the treatment may be observed by reference to CD31 and TRAP staining of the fracture site. Generally the expression of these molecules is expected. Further a callus may be formed, although soft tissue is unlikely to have formed by the 3 week end point. Preferably the treatment should lead to normal progression of endochondral bone healing. This involves a cartilaginous soft callus being progressively replaced by woven bone, which is then remodelled into lamellar/cortical bone.

The effective amount of the tropoelastin may be expected to vary depending upon the circumstances in which bone formation is required. It would be well within the skill of persons skilled in the art to adjust the amount appropriately to obtain optimal results. It is, however, expected that generally the effective amount of the agent will be in the range of 0.1 to 100,000 µg per kg of body weight, more preferably between 1 and 10,000 µg per kg of body weight, and most preferably between about 10 and 1,000 µg.

In certain embodiments the tropoelastin may be provided in doses of from about 0.5 mg to 2000 mg, preferably from 0.5 to 100 mg, more preferably from 1 to 50 mg.

C. Formulations

C.1 Tropoelastin, the Active Agent for Inducing Bone Formation

The tropoelastin utilised in the present invention for stimulating or inducing or promoting bone formation or production may be obtained by purification from a suitable source (eg from humans or other animals) or produced by standard recombinant DNA techniques such as is described in, for example, Maniatis, T. et al., [8].

Recombinant tropoelastin may incorporate modifications (eg amino acid substitutions, deletions, and additions of heterologous amino acid sequences), thereby forming tropoelastin analogues which may, for example, enhance biological activity or expression of the respective protein.

In a preferred embodiment, the methods of the invention utilise the SHELδ26A analogue (WO 1999/03886) [9] for the various applications described herein including for inducing or promoting bone growth, for increasing anabolism of bone, for increasing bone density or volume, or for fracture repair, or correcting a defect or void in bone tissue. The amino acid sequence of SHELδ26A is shown in SEQ ID No: 1 (see also FIG. 9). In alternative embodiments, the tropoelastin isoform is the SHEL isoform (WO 1994/14958) or a protease resistant derivative of the SHEL or SHELδ26A isoforms (WO 2000/0403).

Tropoelastin analogues generally have a sequence that is homologous to human tropoelastin sequence. Percentage identity between a pair of sequences may be calculated by the algorithm implemented in the BESTFIT computer program [10]. Another algorithm that calculates sequence divergence has been adapted for rapid database searching and implemented in the BLAST computer program [11]. In comparison to the human sequence, the tropoelastin polypeptide sequence may be only about 60% identical at the amino acid level, 70% or more identical, 80% or more identical, 90% or more identical, 95% or more identical, 97% or more identical, or greater than 99% identical.

Conservative amino acid substitutions (e.g., Glu/Asp, Val/Ile, Ser/Thr, Arg/Lys, Gln/Asn) may also be considered when making comparisons because the chemical similarity of these pairs of amino acid residues are expected to result in functional equivalency in many cases. Amino acid substitutions that are expected to conserve the biological function of the polypeptide would conserve chemical attributes of the substituted amino acid residues such as hydrophobicity, hydrophilicity, side-chain charge, or size.

The codons used may also be adapted for translation in a heterologous host by adopting the codon preferences of the host. This would accommodate the translational machinery of the heterologous host without a substantial change in chemical structure of the polypeptide.

Recombinant forms of tropoelastin can be produced as shown in WO 1999/03886.

C.2 Formulations Comprising Tropoelastin

It will be understood that the tropoelastin is provided in the formulations of the invention for the purpose of exploiting the biological activity of tropoelastin in inducing bone formation. In this context, tropoelastin is an active ingredient of a tropoleastin—containing composition for the induction of bone formation.

In a particularly preferred embodiment, the only active ingredient or agent for inducing bone repair in a formulation or composition of the invention is tropoelastin. In this embodiment, the formulation does not contain cells such as osteocytes or factors such as BMPs for inducing bone formation.

As discussed above, in some embodiments at least some tropoelastin contained in a formulation according to the invention is not cross linked, bonded or otherwise covalently attached to other components of the composition or formulation, for example, not attached to a scaffold or matrix. This enables at least some, if not all tropoelastin provided in these formulations to be released from the composition to tissue at the site of bone or bone related tissue that requires repair, thereby enabling the tropoelastin to stimulate the tissue elements at that site for bone production.

Preferably, at least some of the tropoelastin provided in the formulation is substantially monomeric (i.e., is not intra-molecularly cross-linked to any significant extent with other components of the formulation) such that the tropoelastin that is provided to the site of injury is also monomeric and may be released from the formulation to the site requiring bone production or formation.

In one embodiment, the tropoelastin provided in the formulation consists of monomers that are not covalently cross-linked.

In yet a further embodiment, the tropoelastin in the formulation may comprise both cross-linked and non-cross-linked forms of the protein, but will typically contain more non-cross-linked forms of the protein.

In one embodiment, no more than about 50% of the tropoelastin contained in the formulation is cross-linked with a biomolecule and/or biopolymer, such as a saccharide-containing molecule, for example, an oligosaccharide, polysaccharide, or derivatives thereof. In other embodiments, no more than about about 40%, 30%, 20%, 10%, or 5% of the tropoelastin is cross-linked.

In certain embodiments, the number of tropoelastin molecules not incorporated into a cross-linked protein matrix or complex and left unbound is preferably at least 50%, 60%, 70%, 80%, 90% or 95%.

In certain embodiments, the tropoelastin has a specified degree of purity with respect to the amount of tropoelastin in a composition for administration, as compared with amounts of other proteins or molecules in the composition. In one embodiment, the tropoelastin is in a composition that has at least 75% purity, preferably 85% purity, more preferably more than 90% or 95% purity. Fragments of tropoelastin, i.e., truncated forms of a tropoelastin isoform that arise unintentionally through tropoelastin manufacture may be regarded as an impurity in this context.

It will further be understood that in certain embodiments the tropoelastin may be provided in the form of a composition that consists of or consists essentially of tropoelastin, preferably a full length isoform of tropoelastin. In alternative embodiments, the tropoelastin will be at least 65% of the length of the relevant tropoelastin isoform, more than 80% of the full length, more than 90% or more than 95% of the full length.

Typically, the tropoelastin formulations for use in accordance with the present invention have a tropoelastin concentration greater than about 1.5 mg/mL (although lower concentrations may also be used). For example, a tropoelastin formulation having a concentration of tropoelastin from about 1.5 mg/mL to about 400 mg/mL is preferable. More preferably, the formulation will have a tropoelastin concentration between about 5 mg/mL to about 300 mg/mL yet more preferably about 10 mg/mL to about 200 mg/m L.

Typically a formulation of the invention contains a component defining the mechanical, or physical properties of the formulation. Examples of these properties, in the context of hydrogels as examples of formulations of the invention are described below. Further described are examples of components which are generally water binding, long chain or polymeric molecules including hyaluronic acid.

C.3 Hydrogels

Typically, a hydrogel for use according to the invention comprises:
polymeric hydrophilic molecules forming a scaffold and imbuing the hydrogel with mechanical properties described below;
water; and
tropoelastin for inducing or promoting bone production or formation.

As described below, examples of polymeric hydrophilic molecules include carboxymethyl cellulose, hydroxypropyl cellulose, hydroxypropyl methylcellulose, hyaluronic acid, xanthan gum, guar gum, β-glucan, alginates, carboxymethyl dextran.

In one embodiment, a hydrogel according to the invention may provide for a tensile strength of from 100 kPa to 2 MPa. Tensile strength is usually defined as the maximum stress that a material can withstand while being stretched or pulled before the material's cross-section starts to significantly stretch. A person skilled in the art will be aware of suitable methods to test the ultimate strength of a material. The hydrogel of the present invention can have an ultimate strength ranging from about 10 to about 45 kPa (for example, about 12 to about 40 kPa).

In another embodiment the hydrogel has a compression strength of from 50 kPa to 700 kPa. Compressive strength is the capacity of a material or structure to withstand axially directed pushing forces. It provides data (or a plot) of force vs deformation for the conditions of the test method. By definition, the compressive strength of a material is that value of uni-axial compressive stress reached when the material fails completely. The compressive strength is usually obtained experimentally by means of a compressive test. The apparatus used for this experiment is the same as that used in a tensile test. However, rather than applying a uni-axial tensile load, a uni-axial compressive load is applied. As can be imagined, the specimen is shortened as well as spread laterally. Compressive strength is often measured on a universal testing machine; these range from very small table-top systems to ones with over 53 MN capacity. Measurements of compressive strength are affected by the specific test method and conditions of measurement.

Compressive strength of the hydrogels can be determined using cyclic loading at a given strain level (for example, 5%, 10%, 15%, 20%, 25%, 30%, 35%, 40%, 45%, 50%, 55%, 60%, 65%, 70% or 75% strain level). The compressive modulus of the hydrogels can range from about 1 kPa to about 500 kPa.

Under compression, the hydrogels can lose energy. Energy loss can range from about 5% to about 50%. In some embodiments, energy loss can be from about 10% to about 40%, from about 20% to about 35% (for example, 23±3.2% or 24.1±7%), or from about 25% to about 30% (for example, 30.5±6.4 or 26.9±2.3).

In one embodiment, the strain at break of the hydrogel between about 130 and about 420 kPa. The strain at break test is performed by stretching samples until they break and determining the strain at breaking point from the strain/stress curves.

In certain embodiments, the tropoelastin formulations for use in accordance with the present invention, may have an elastic modulus of between about 500 Pa to about 50 Pa, about 450 Pa to about 100 Pa, about 400 Pa to about 125 Pa; about 400 Pa to about 150 Pa, or about 385 Pa to about 150 Pa. The elastic modulus will vary depending on the concentration and components used.

In certain embodiments, the hydrogels may have an extrudable length, that is substantially coherent and substantially holds together without support, of at least about 5 cm, 10 cm, 12 cm, 15 cm, 18 cm, 20 cm, or 25 cm when extruded through a 25G needle. Certain embodiments may have an extrudable length, that is substantially coherent and substantially holds together without support, of at least about 5 cm, 10 cm, 12 cm, 15 cm, 18 cm, 20 cm, or 25 cm when extruded through a 27G needle. Certain embodiments may have an extrudable length, that is substantially coherent and substantially holds together without support, of at least about 5 cm, 10 cm, 12 cm, 15 cm, 18 cm, 20 cm, or 25 cm when extruded through a 30G needle or 31G needle.

Certain embodiments may have an extrudable length of at least about 5 cm, 10 cm, 12 cm, 15 cm, 18 cm, 20 cm, or 25 cm through a fine gauge needle.

The hydrogels for use in accordance with the present invention may also be swellable. The term "swellable" refers to hydrogels that are substantially insoluble in a swelling agent and are capable of absorbing a substantial amount of the swelling agent, thereby increasing in volume when contacted with the swelling agent. As used herein, the term "swelling agent" refers to those compounds or substances which produce at least a degree of swelling. Typically, a swelling agent is an aqueous solution or organic solvent, however the swelling agent can also be a gas. In some embodiments, a swelling agent is water or a physiological solution, for example phosphate buffer saline, or growth media.

In some embodiments, the hydrogel comprises a swelling agent. In some embodiments, the hydrogel can contain over 50% (w/v), over 60% (w/v), over 70% (w/v), over 80% v, over 90% (w/v), over 91% (w/v), over 92% (w/v), over 93% (w/v), over 94% (w/v), over 95% (w/v), over 96% (w/v), over 97% v, over 98% (w/v), over 99% (w/v), or more of the swelling agent.

The term "swelling ratio" is used herein to mean weight of swelling agent in swollen hydrogel per the dried weight of the hydrogel before swelling. For example, the swelling ratio can range from about 1 to about 10 grams of swelling agent per gram of the tropoelastin in the hydrogel. In some embodiments, the swelling ratio can be from about 1 to about 5 grams of swelling agent per gram of the tropoelastin in the hydrogel.

In some embodiments, the swelling ratio can be about 1.25, about 1.5, about 1.75, about 2, about 2.25, about 2.5, about 2.75, about 3, about 3.25, about 3.5, about 3.75, about 4, about 4.25, about 4.5, about 4.75 or about 5 grams of swelling agent per gram of tropoelastin in the hydrogel. In some embodiments, the swelling ratio can be 1.2±0.2, 2.3±0.3, or 4.1±0.3 grams of swelling agent per gram of tropoelastin in the hydrogel.

In a preferred embodiment, the tropoelastin formulations used in accordance with the present invention, are hydrogels which have suitable persistence properties such that the formulation is maintained at the site of delivery for a sufficient period to enable release of tropoelastin at multiple times so that tropoelastin can exert its biological effect. In other words, the hydrogel will typically have a 'residence time' at the site of delivery of more than 1 week, preferably at least 2 weeks.

In certain embodiments, a hydrogel generally has a functionality (i.e. water-binding, mechanical strength, phase-transition and cross-linking) suitable for application as a bone filler for inducing or promoting bone wound repair. According to the invention, this functionality principally arises from components other than tropoelastin. These components may be polymeric and are described in more detail below. The tropoelastin is provided in the hydrogel for the purposes of promoting bone formation.

The skilled person will appreciate that hydrogels can be used as scaffolds for tissue engineering applications because of their biocompatibility and high water content, which resemble the natural tissue microenvironment. Further, the skilled person will appreciate that various methods exist for modifying the mechanical properties of the hydrogels, including the extensibility of the hydrogels to facilitate increased residence time at the site of delivery, and thereby providing for an increased release time for the active agent (in this case, according to the invention, tropoelastin) contained within the hydrogel.

In one embodiment, after formation of the hydrogel, the hydrogel may be dried to provide a polymeric substrate including the tropoelastin. In this embodiment, the polymeric substrate is the component for providing structure and function referred to above. This dehydrated composition may then be sold for use in bone repair and re-hydrated in sterile conditions before clinical use.

The hydrogels utilised in the invention have properties of flow that enable injection to the site of bone defect or wound. This is a distinguishing feature over other elastomeric bone fillers. Further to injection capability, this enables the hydrogel to flow across the surface of the relevant bone site, providing extensive and complete contact with the bone surface, thereby improving or accelerating bone repair.

In one embodiment, the phase transition characteristics of the components that form the hydrogel may enable the hydrogel to set at body temperature, thereby ostensibly forming a substrate or graft that is in extensive contact with bone tissue across the wound site. The hydrogels for use in accordance with the present invention are distinguished from other elastomeric bone fillers which are placed at the wound site as a solid pre-fabricated structure that therefore has limited and not extensive contact with the bone surface across the wound site.

In certain embodiments, the formulations of the invention herein may have properties of flow at 20 to 37° C., preferably less than 45° C. enabling delivery of the formulation to the site by injection.

Typically a hydrogel utilised in the invention for bone wound repair is one having properties of flow enabling injection of the hydrogel through a needle with a gauge of between 18G and 32G, preferably 26G to 31G, more preferably 27G with minimal thumb backpressure. This injection pressure is less than 350 kPa which is well below the acceptable pressure range for disposable syringes.

In certain preferred embodiments, the hydrogels of the present invention include Hyaluronic acid (HA) for use as a scaffold. In these circumstances, the HA functions to provide certain mechanical properties to the hydrogel, allowing the tropoelastin to remain substantially free (un-crosslinked), such that the tropoelastin has the ability to function as a biological factor, stimulating and inducing bone formation at the site where the hydrogel is provided.

In certain embodiments, where the hydrogel includes tropoelastin and hyaluronic acid, the mass ratio of tropoelastin to hyaluronic acid is 0.1:1 to about 500:1, preferably, about 0.2:1 to about 100:1.

In yet further embodiments, the hydrogel may comprise HA in a concentration of between about 0.1% to about 15%. In certain embodiments, the hydrogel may comprise the HA in a concentration of between about 0.1% to about 10%.

The hydrogel may comprise derivatised HA or underivatised HA, to control the extent to which the HA crosslinks with itself and/or the monomeric protein.

In certain embodiments, the HA may comprise, at least one linkable moiety, such as at least one cross-linkable moiety, for example, a carboxyl group, a hydroxyl group, an amine, a thiol, an alcohol, an alkene, an alkyne, a cyano group, or an azide, and/or modifications, derivatives, or combinations thereof.

In certain embodiments, the HA may comprise, a spacer group, such that the spacer group is capable of linking to the same and/or a second molecule, for example, a second biomolecule or biopolymer.

The HA used in the hydrogel may be in the range of about 100 to 300 saccharide units or residues, for example around 200 saccharide units or residues. In other embodiments, hyaluronic acid may be used in the range of 200 to 20,000 saccharide units or residues.

In certain embodiments, the HA may be low or high molecular weight, and the choice of which will vary depending on the skilled person's intentions for modifying the viscosity of the hydrogel. For example, use of lower molecular weight hyaluronic acid allows the hyaluronic acid to be modified, precipitated and washed and the hyaluronic acid remains a reasonably low viscous solution that may be readily used as the cross-linking agent. Using higher molecular weight polysaccharides may provide additional handling issues (e.g., viscous solution, problems with mixing, aeration etc) but, in certain embodiments, a wide range of molecular weights may be used to achieve the desired results.

In certain embodiments, the HA may be activated and/or modified with an activating agent, such as EDC or allylglycidyl ether, and/or modifying agent, such as NHS, HOBt or Bromine.

The term "hyaluronic acid" or "HA" may include hyaluronic acid and any of its hyaluronate salts, including, for example, sodium hyaluronate (the sodium salt), potassium hyaluronate, magnesium hyaluronate, and calcium hyaluronate. Hyaluronic acid from a variety of sources may be used herein. For example, hyaluronic acid may be extracted from animal tissues, harvested as a product of bacterial fermentation, or produced in commercial quantities by bioprocess technology.

In one embodiment, the hydrogels of the present invention include the polymer poly(NIPAAm-co-NAS-co-(HEMA-PLA)-co-OEGMA) (PNPHO; preferably a polymer having 73% N-isopropyl acrylamide, 8% lactide, 5% ethylene glycol, 14% N-acryloxysuccinimide formulation).

In the PNPHO-tropoelastin hydrogels, the tropoelastin and PNPHO have defined roles. The tropoelastin serves as the source of bioactive signalling for bone regeneration, and the PNPHO acts as a scaffold to provide properties of persistence to the hydrogel.

The PNPHO polymer is chemically bonded with tropoelastin to (a) adjust the physicochemical properties of this biopolymer for bone applications, (b) to impart rapid thermosetting to the hydrogel filler to confine it locally, and (c) to impart bioresorption properties to the injectable hydrogels. The combination of these two main segments results in the formation of the new class of smart bone fillers with a range of favourable properties for bone healing.

The skilled person will appreciate that in modifying the relative proportions of tropoelastin to PNPHO, it is possible to modify the extent to which hydrogel provides tropoelastin in substantially free form. In other words, by decreasing the proportion of PNPHO (and increasing the overall proportion of tropoelastin) in the hydrogel, it is possible to increase the amount of free tropoelastin in the hydrogel, which is desirable for the present invention, since the tropoelastin needs to be able to diffuse from the hydrogel to exert is physiological and biological effect.

In one embodiment, the final molar ratio of tropoelastin to PNPHO in the hydrogel is 10 (tropoelastin): 1 (PNPHO). In a preferred embodiment, the final molar ratio of tropoelastin to PNPHO in the hydrogel is 5:1, 4:1, 3:1, 2:1, more preferably 1:1.

Suitable polysaccharides which may also be included in the hydrogels include carboxy cellulose, carboxymethyl cellulose, hydroxymethyl cellulose, hydroxypropyl cellulose (HPC), hydroxypropyl methylcellulose (HPMC), hydroxy-propylcellulosecarboxymethyl amylose ("CMA"), xanthan gum, guar gum, β-glucan, alginates, carboxymethyl dextran, a glycosaminoglycan derivative, chondroitin-6-sulfate, dermatin sulfate, polylactic acid (PLA), or biomaterials such as polyglycolic acid (PGA), poly(lactic-co-glycolic) acid (PLGA), tricalcium phosphate (TCP), 1-hydroxyapatite (PAH), and their pharmaceutically acceptable salts. Alternatively, the polysaccharide may be a pectin or a derivative thereof, including linear and branched polysaccharides.

When the scaffold agents used in the tropoelastin hydrogels is carboxymethylcellulose or xanthan gum, the agent may be provided in an amount of from about 0.01 to 10 percent (w/v), preferably in an amount of from 0.5 to 3.5 percent (w/v).

The scaffold may be a cross-linked or uncross-linked polysaccharide typically having a substitution or additional side chain.

Additional scaffold may include scaffolds derived from polymethacrylates, polyethylene glycols and (block) copolymers with polyethylene glycol subunits (for example Poloxamer 188 and Poloxamer 407). Alternative agents included in the hydrogels include surfactants such as sodium lauryl sulfate and polysorbates, or pantothenol, polyethylene glycols, xanthan gum, guar gum, polysorbate 80, N-acetylglucosamine and their pharmaceutically acceptable salts.

Further aspects of the present invention and further embodiments of the aspects described in the preceding paragraphs will become apparent from the following description, given by way of example and with reference to the accompanying drawings.

EXAMPLES

Example 1 Biomechanical Properties of Tropoelastin Gel

An ex vivo, clean sharp tibia fracture model was used to assess the biomechanical properties of tropoelastin provided in a poly(NIPAAm-co-NAS-co-(HEMA-PLA)-co-OEGMA) (PNPHO) hydrogel (TE-PNPHO hydrogel). Briefly, a TE-PNPHO hydrogel was injected into clean, fresh cadaver sheep tibia fracture. The tropoelastin hydrogel adhered to the bone and filled the fracture, making contact with the fracture surfaces at and between the periosteal and endosteal margins, as shown in FIG. 1.

The test was repeated for 6 independent tibia fractures, and the mechanical strengths of the bones were measured in each case. Surprisingly, 80% of the strength of the bone was recovered following injection of the tropoelastin hydrogel. This performance was modelled on the injectable's tissue-adhesiveness properties, combined with the viscoelastic performance of the hydrogels. Control measurements were also performed and confirmed that this effect was due to the presence of tropoelastin, since the mechanical performance was not restored in the absence of tropoelastin.

Figure 2:
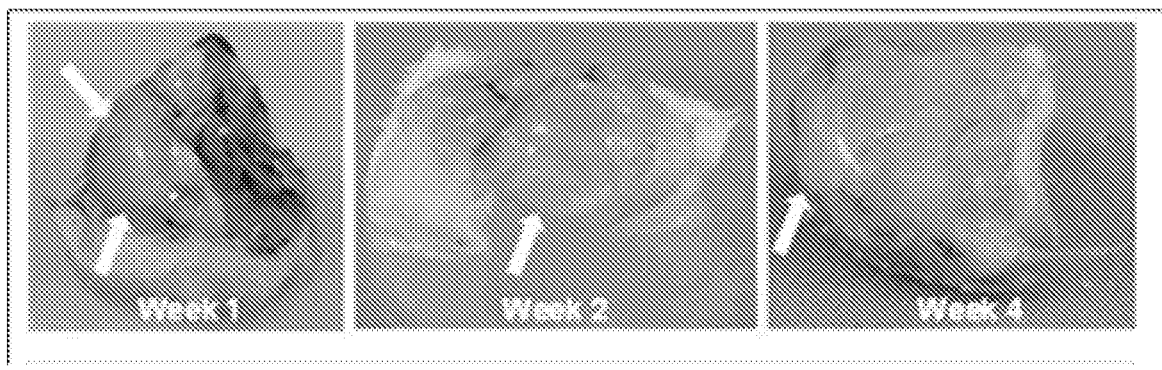

Example 2—Iniectability, Cytocompatability and Cellular Infiltration of Tropoelastin Gel In vivo studies were conducted to assess the injectability, cytocompatibility and stability of the tropoelastin-PNPHO hydrogels used in accordance with the instant invention. The high tissue adhesive properties and fast gelation time of the tropoelastin-PNPHO eradicated the need for sutures or any other physical supports to constrain the injected hydrogel in place. The hydrogels were retained at the injection site for up to 8 weeks (FIG. 2). The explanted samples were used to histochemically assess the cytocompatiblity and in vivo biological properties of the implants at different time points.

Figure 3:
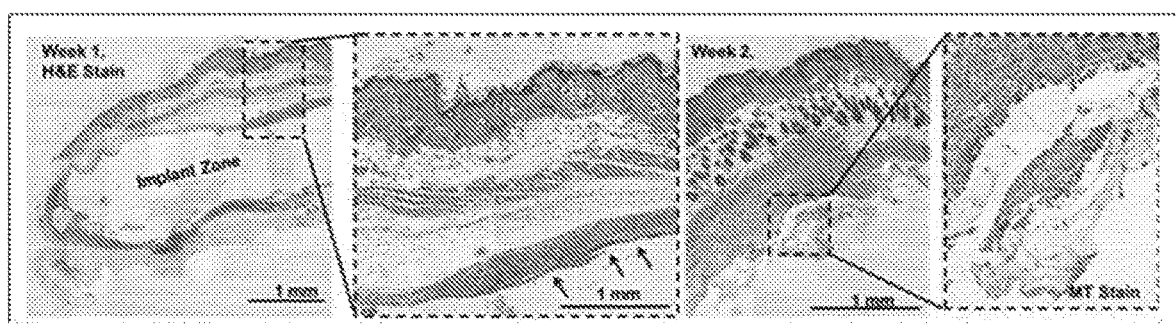
FIG. 3—Haematoxylin and eosin (H & E) staining of implants after 1 and 2 weeks following injection. The results of the staining showed a reduction in inflammatory response after 1 week (indicated with an arrow). Milligan's trichome (MT) staining of samples at week 2 demonstrates fibroblast infiltration and collagen deposition.

Results from haematoxylin and eosin (H&E) stained samples showed outstanding cytocompatible properties of the tropoelastin hydrogels. Only a mild inflammatory response to tropoelastin was observed one week injection. The H&E staining of samples, as shown in FIG. 3 demonstrated that the fibrous tissues around the hydrogel had settled in the period one week to two weeks post-surgery. Milligan's trichrome (MT) staining of the week two samples in FIG. 3 shows dermal fibroblast infiltration and de novo collagen deposition within the tropoelastin hydrogels.

Example 3—Sheep Model of Bone Repair

Figure 4:
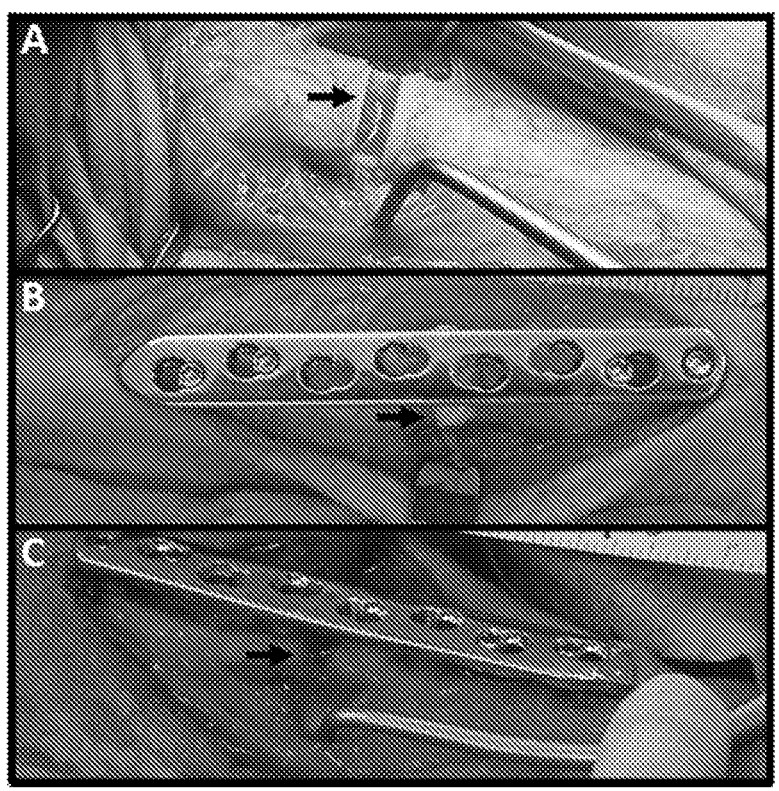
FIG. 4—Osteotomy in ovine model of bone repair (A) and following treatment with injectable tropoelastin-containing gels (B and C). Black arrows indicate the osteotomy site.

The ovine model was accomplished as an osteotomy from Anterior to Posterior surfaces through the tibial shaft. All sheep were 2 to 3 years of age. Following anaesthesia, an oscillating bone saw was used to resect a 3 mm segment of the right mid diaphyseal tibia of each sheep (FIG. 4A). The injured bone site was stabilised with a standard 13 mm long, 3.5 mm bone plate and 2.5 mm offset secured to the non-drilled aspect of the tibial corticalis by appropriate screws (FIG. 4). The bone gap was then filled with tropoelastin containing hydrogels or left empty as the negative control. The tropoelastin-containing hydrogels were either a PNPHO-based hydrogel (TE-PNPHO hydrogel) (FIG. 4B) or a HA-based hydrogel (TE-HA hydrogel) (FIG. 4C). Tropoelastin-containing gels were readily injected into the osteotomy site, where they completely filled the gap. The surgical wound was closed with 3/0 polydioxanone subcutaneous and intradermal continuous sutures.

X-ray computed tomography (CT) scans were conducted at 0, 4 and 8 weeks post-surgery. The specimen were harvested at 8 weeks post-surgery for histological analyses.

Results

A. Controls

Selection of the specimen was difficult as the bone fell apart when attempting harvesting of the osteotomy.

Figure 5:
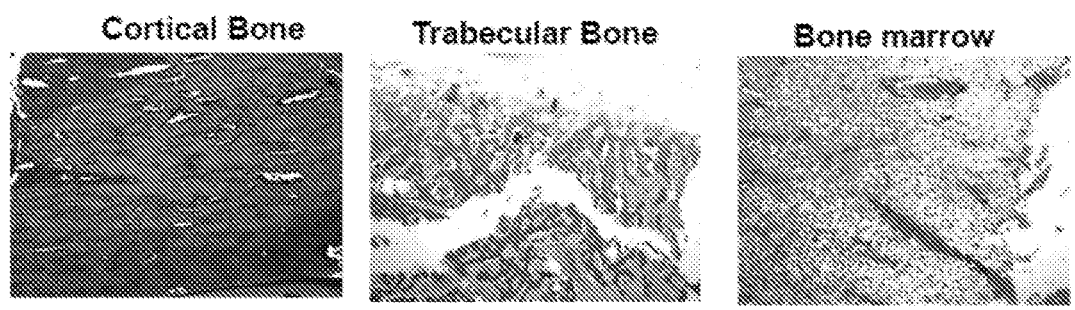
FIG. 5—Ovine model of bone repair. A: the three different types of tissues detected: cortical bone, trabecular bone and bone marrow. B: Control, MT stained at 8 weeks. C: Test samples (treated with tropoelastin gel) MT stained at 8 weeks. D: Immature woven bone was formed in the control samples and was denser at the periosteal-facing surfaces as compared with the endosteum region. Bone marrow was present at the endosteum region. E. Strong cortical bone was formed at the endosteum end in the tropoelastin gel-treated samples. The osteotomy gap was decreased from 3 mm to 1.8 mm.
Figure 5:
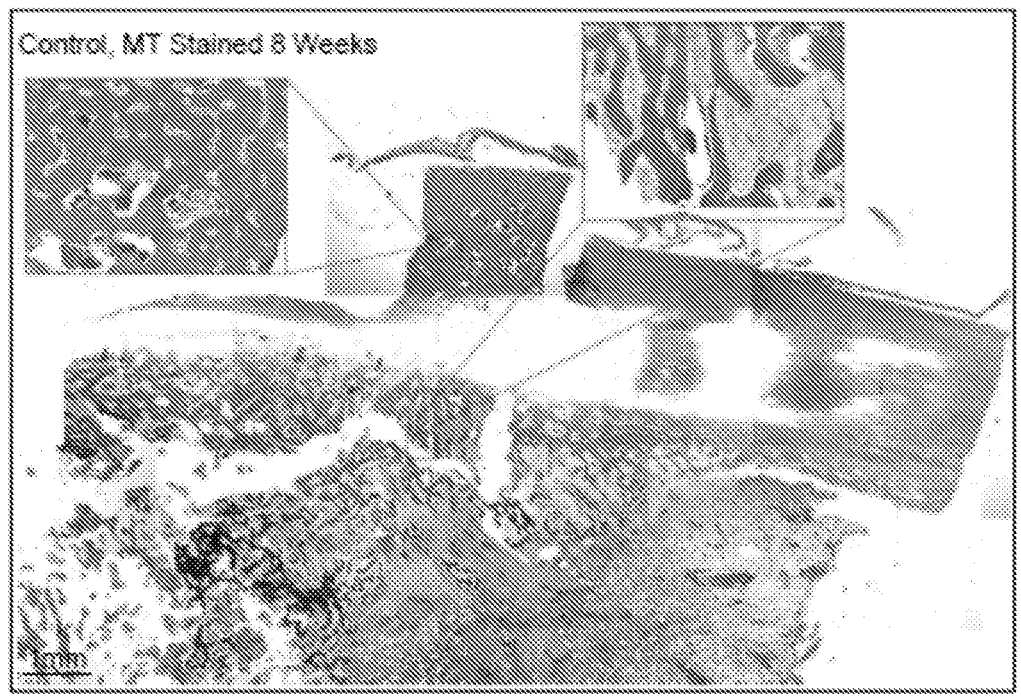
Figure 5:
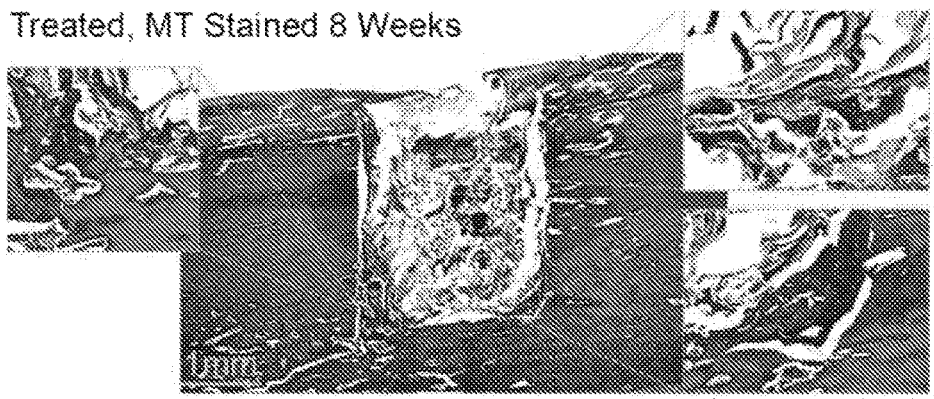
Figure 5:
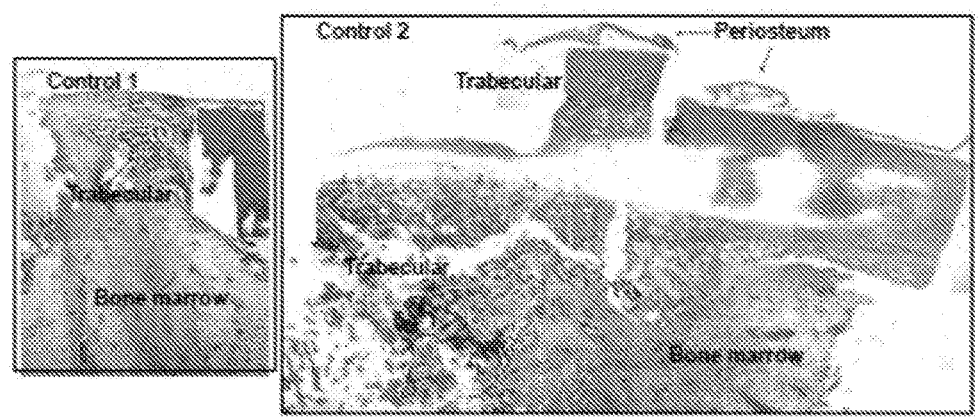
Figure 5:
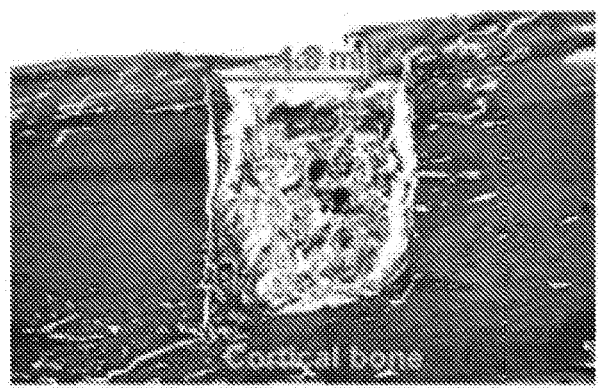

Microscopic features observed: periosteum was mildly thickened by hyperplastic cells with minimal amounts of intercellular collagenous matrix (FIG. 5) The defect in the bone was filled with immature woven bone with inter trabecular spaces that were filled with undifferentiated vascular tissue. Mild remodelling of the seams of the osseous trabeculae was present as a sprinkling of osteoclastic resorption sites and plump osteoblasts lining some of the osseous seams.

Immature woven bone was formed and was denser at the periosteal surfaces as compared with the endosteum region. Bone marrow tissue were present at the endosteum region. The strength of the bone without the mechanical plate was minimal.

B. Test Samples:

Selection of samples was relatively easy as the osteotomy and bone held together as samples were collected/harvested.

Microscopic features observed (FIG. 5): an open well of approximately 5 mm covered by a periosteal layer mostly of fibrous tissue contained a few small osseous trabeculae. The walls of the well were mainly composed of the corticalis from the shaft of the tibia (prior to sawing). Some recently formed bone occurred in the apparent deep corners of the well but most of the well contained open moderately dense fibrovascular tissue with occasional small osseous trabeculae. The floor of the well was approximately 3 mm in thickness of dense reparative compact bone. This arch shaped dense bone appeared to be endosteal derived.

Strong cortical bone was formed at the endosteum region. The formation of cortical bone at the endosteum allows fast recovery of the mechanical strength of the tissue. Some trabecular bone was also observed at the osteotomy site, close to the periosteum. The osteotomy hap was decreased from 3 mm to 1.8 mm. Endosteal compact cortical bone joined the tibial diaphyseal segments. Considerable strength had been achieved by the endosteal reparative bone.

Figure 6:
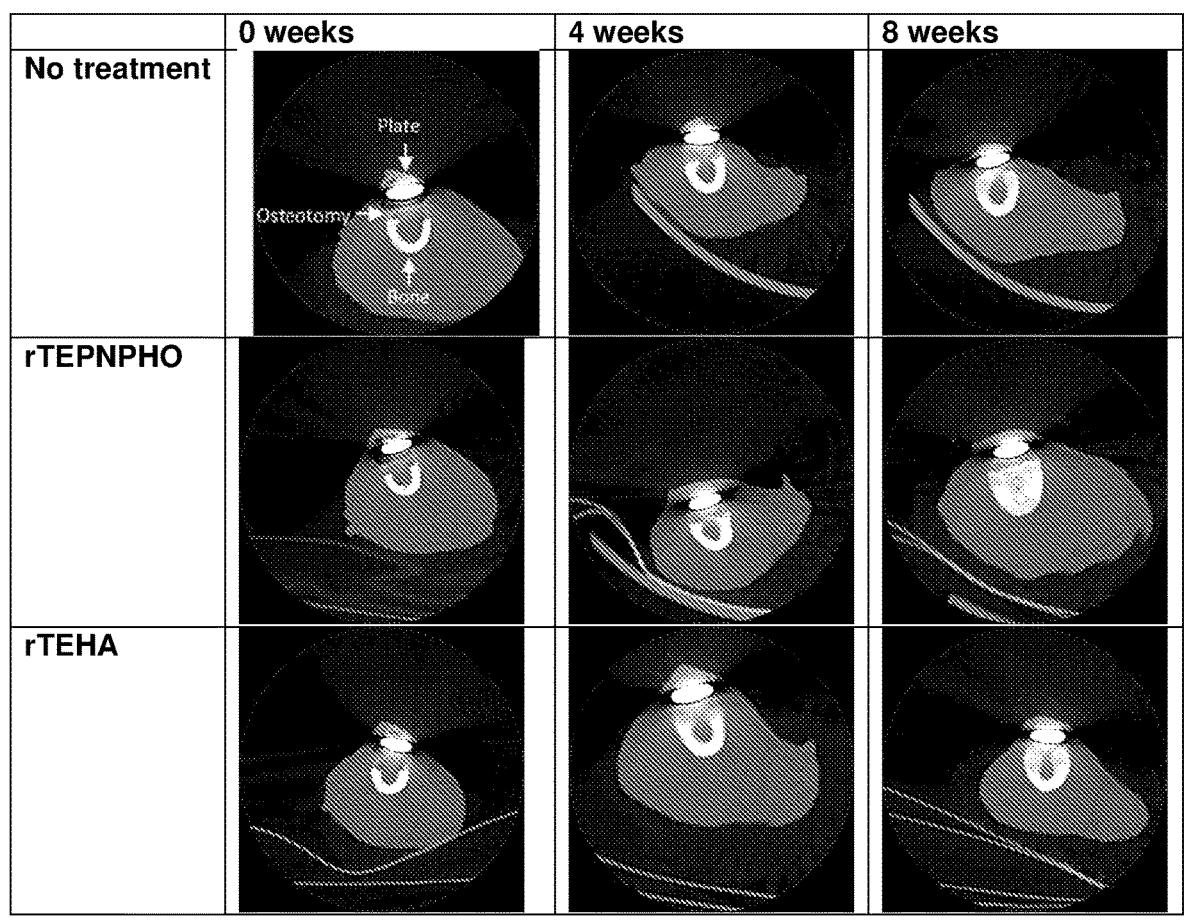
FIG. 6—CT images of osteotomy sites in the ovine model of bone repair. Images taken at 0, 4 and 8 weeks post-surgery and show portion of osteotomy with the largest gap remaining.

CT images of osteotomy sites (FIG. 6) were taken at 0, 4 and 8 weeks post-surgery and show sharp cut lines across the bone immediately after surgery which begin to blur by 4 weeks and fill-in by 8 weeks as the bone repairs. Treatment of the bone defect with tropoelastin-containing gels appeared to both accelerate and enhance bone healing suggesting that the materials are both osteoconductive and osteo inductive.

DISCUSSION

The controls defects were filled with open trabecular bone that occupied the osteotomy to the periosteal fibrous layer and could be traced extending from the marrow tissue. The strength of the bone without the mechanical plate was minimal.

In contrast the test specimens had formed a dense arch of endosteal compact bone joining the tibial diaphyseal segments.

Although much of the osteotomy had not filled with osteogenic tissue considerable strength had been achieved by the endosteal reparative bone. Such allowed the specimen to be harvested without breaking after removal of the mechanical plate and screws.

Example 4—Rabbit Model of Bone Defect Repair

Experimental Design

Animals: New Zealand white rabbits, 7-8 months old, 3.0-4.5 kg. N=6/group.

Groups 1 and 2:

Critical-sized bone defects were made to the medial femoral condyle of animals. Defects were 3 mm diameter, 3 mm depth (full thickness) (FIG. 7A). Defects were injected with cylindrical grafts containing tropoelastin (group 1, test animals) or carrier (group 2, control animals).

Repairs of the defects were assessed at 4 and 8 weeks following injury and injection of the grafts.

Analysis:

Repair of the defects were assessed using imaging techniques (μCT and MRI) and histological analysis (Hematoxylin and eosin to determine normal histological features, Masson's trichome (to assess collagen fibers) and immunohistochemistry (to detect tropoelastin).

Figure 7:
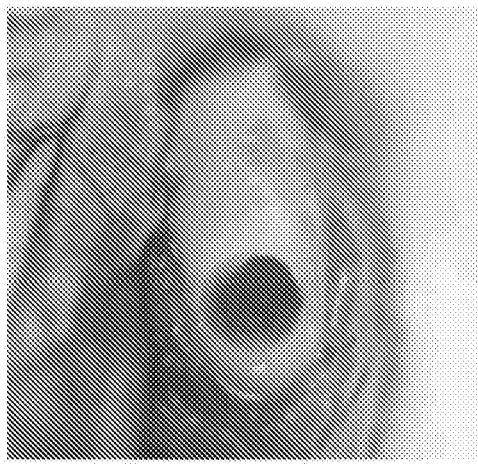
FIG. 7—Rabbit model of critical sized bone defect repair. A=site of injury prior to treatment. B=site of injury following injection of tropoelastin gel at Day 0.
Figure 7:
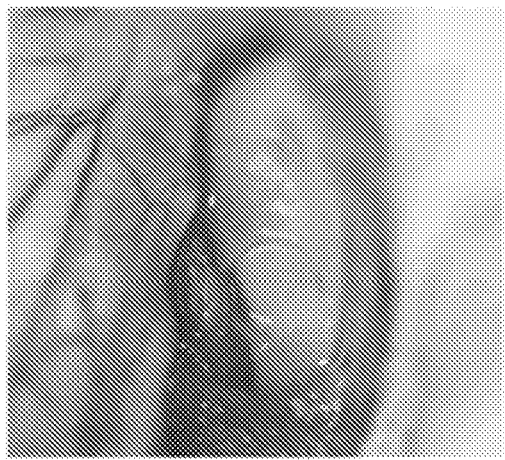
Figure 8:
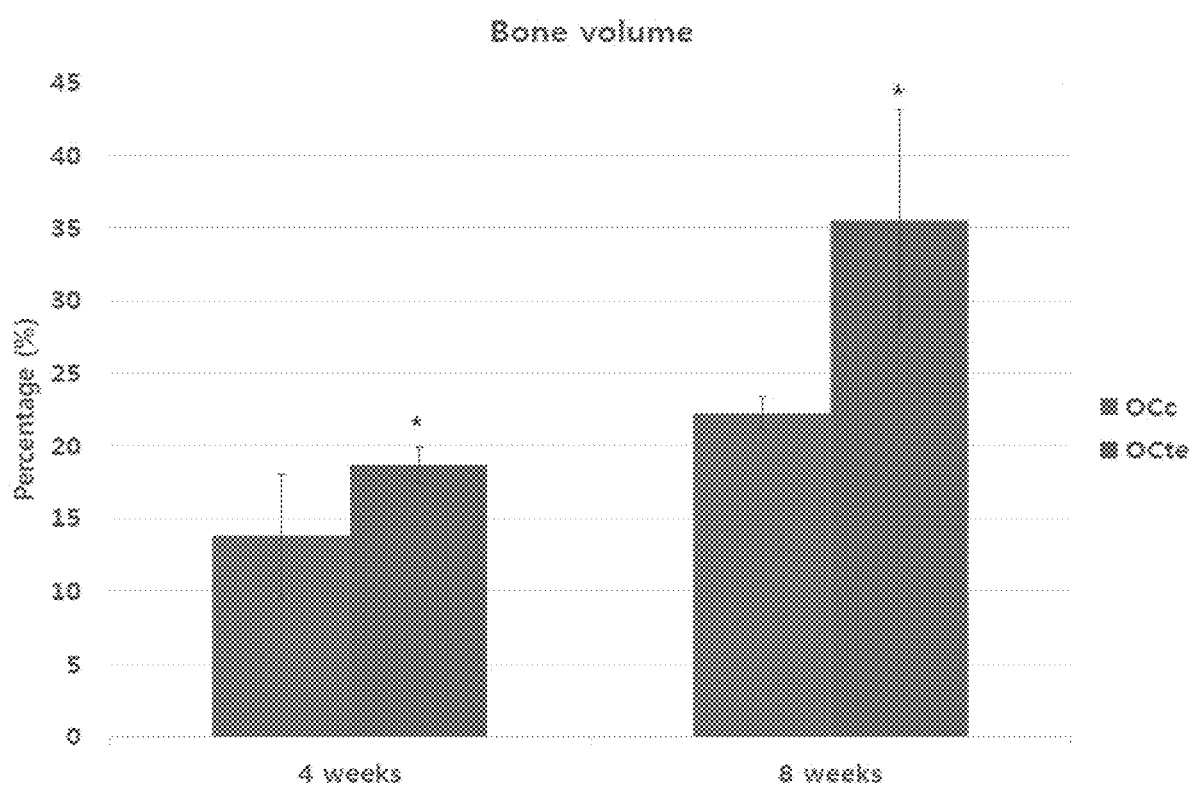
FIG. 8—μCT results, rabbit model of bone defect repair. OCc=control; OCte=treated with tropoelastin. *=differs significantly between the two groups.

Results:

The tropoelastin gel retained at the injection site (FIG. 7). Also, the injection of tropoelastin gel at the site of injury in rabbits resulted in formation of bone. μCT analysis showed an increase in bone volume at weeks 4 and 8 for test animals compared to control animals (FIG. 8). The results from the μCT analysis showed that injection of tropoelastin gel in critical sized bone defects significantly enhanced the tissue regeneration in compared with control groups (empty voids).

Example 5: Synthesis of TE-HA Hydrogels

Hydrogels comprising tropoelastin with hyaluronic acid as a scaffold (TE-HA hydrogels) were made by combining a solution of recombinant human tropoelastin (200 mg/ml) with phosphate buffered saline followed by the addition of derivatised HA, to a final concentration of approximately 50 mg/ml. The combination was mixed thoroughly followed by brief centrifugation to remove air bubbles. The material was left for 30 min at room temperature to formulate. The hydrogel was then filled into a sterile 1 ml syringe in a laminar flow hood.

Similar hydrogels were made in this way, comprising tropoelastin at a final concentration of about 10 mg/ml to 100 mg/ml.

The formulations made in this way all presented with the properties of firm materials which were extrudable through fine gauge 27G needles as coherent threads of 10-20 cm in length.

The tropoelastin hydrogels made in this way contained high levels of non-cross-linked tropoelastin such that the tropoelastin was free to be released from the hydrogel at the site of delivery and to be able to act to promote bone formation.

Tropoelastin hyaluronic acid hydrogels made in this way were utilised in various in vivo experiments and showed increased persistence time, and ability to induce bone formation (as shown in Example 3).

Example 6: Synthesis of TE-PNPHO Hydrogels

Hydrogels comprising tropoelastin with PNPHO as a scaffold (TE-PNPHO hydrogels) were made by combining tropoelastin and PNPHO to a final concentration of 30 mg/ml tropoelastin and 10 mg/ml PNPHO (equivalent to a 1:1 molar ratio).

In one method PNPHO copolymer was dissolved in PBS for 24 hr. Tropoelastin solution was added to PNPHO solution and incubated at 4° C. for another 24 hr.

In an alternative, dissolution of PNPHO and protein conjugation were conducted at the same time.

In a third method PNPHO was dissolved and conjugated with naturally derived protein on a shaker.

In a further method PNPHO-tropoelastin conjugate powder was formed by freeze drying PNPHO-tropoelastin solution. The conjugate powder was dissolved in PBS on a shaker to form the final polymeric solution.

The tropoelastin-PNPHO solutions formed with different techniques were converted to hydrogels by increasing the temperature to 37° C. The tropoelastin hydrogels made in this way contained high levels of non-cross-linked tropoelastin such that the tropoelastin was free to be released from the hydrogel at the site of delivery and to be able to act to promote bone formation. These hydrogels were utilised in various in vivo experiments and showed increased persistence time, and ability to induce bone formation (as shown in Examples 1-4).

```
SEQ ID NO: 1 SHELo26A amino acid sequence:
Gly Gly Val Pro Gly Ala Ile Pro Gly Gly Val Pro Gly Gly Val Phe Tyr Pro Gly Ala Gly Leu Gly Ala Leu Gly Gly Gly Ala Leu Gly Pro Gly Gly Lys Pro Leu Lys Pro Val Pro Gly Gly Leu Ala Gly Ala Gly Leu Gly Ala Gly Leu Gly Ala Phe Pro Ala Val Thr Phe Pro Gly Ala Leu Val Pro Gly Gly Val Ala Asp Ala Ala Ala Ala Tyr Lys Ala Ala Lys Ala Gly Ala Gly Leu Gly Gly Val Pro Gly Val Gly Gly Leu Gly Val Ser Ala Gly Ala Val Val Pro Gln Pro Gly Ala Gly Val Lys Pro Gly Lys Val Pro Gly Val Gly Leu Pro Gly Val Tyr Pro Gly Gly Val Leu Pro Gly Ala Arg Phe Pro Gly Val Gly Val Leu Pro Gly Val Pro Thr Gly Ala Gly Val Lys Pro Lys Ala Pro Gly Val Gly Gly Ala Phe Ala Gly Ile Pro Gly Val Gly Pro Phe Gly Gly Pro Gln Pro Gly Val Pro Leu Gly Tyr Pro Ile Lys Ala Pro Lys Leu Pro Gly Gly Tyr Gly Leu Pro Tyr Thr Thr Gly Lys Leu Pro Tyr Gly Tyr Gly Pro Gly Gly Val Ala Gly Ala Ala Gly Lys Ala Gly Tyr Pro Thr Gly Thr Gly Val Gly Pro Gln Ala Ala Ala Ala Ala Ala Ala Lys Ala Ala Ala Lys Phe Gly Ala Gly Ala Ala Gly Val Leu Pro Gly Val Gly Gly Ala Gly Val Pro Gly Val Pro Gly Ala Ile Pro Gly Ile Gly Gly Ile Ala Gly Val Gly Thr Pro Ala Ala Ala Ala Ala Ala Ala Ala Ala Lys Ala Ala Lys Tyr Gly Ala Ala Gly Leu Val Pro Gly Gly Pro Gly Phe Gly Pro Gly Val Val Gly Val Pro Gly Ala Gly Val Pro Gly Val Gly Val Pro Gly Ala Gly Ile Pro Val Val Pro Gly Ala Gly Ile Pro Gly Ala Ala Val Pro Gly Val Val Ser Pro Glu Ala Ala Ala Lys Ala Ala Lys Ala Ala Lys Tyr Gly Ala Arg Pro Gly Val Gly Val Gly Gly Ile Pro Thr Tyr Gly Val Gly Ala Gly Phe Pro Gly Phe Gly Val Gly Val Gly Gly Ile Pro Gly Val Ala Gly Val Pro Ser Val Gly Val Pro Gly Val Gly Gly Val Pro Gly Val Gly Ile Ser Pro Glu Ala Gln Ala Ala Ala Ala Ala Lys Ala Ala Lys Tyr Gly Val Gly Thr Pro Ala Ala Ala Ala Ala Lys Ala Ala Ala Lys Ala Ala Gln Phe Gly Leu Val Pro Gly Val Gly Val Ala Pro Gly Val Gly Val Ala Pro Gly Val Gly Val Ala Pro Gly Val Gly Leu Ala Pro Gly Val Gly Val Ala Pro Gly Val Gly Val Ala Pro Gly Val Gly Val Ala Pro Gly Ile Gly Pro Gly Gly Val Ala Ala Ala Lys Ser Ala Ala Lys Val Ala Ala Lys Ala Gln Leu Arg Ala Ala Ala Gly Leu Gly Ala Gly Ile Pro Gly Leu Gly Val Gly Val Gly Val Pro Gly Leu Gly Val Gly Ala Gly Val Pro Gly Leu Gly Val Gly Ala Gly Val Pro Gly Phe Gly Ala Val Pro Gly Ala Leu Ala Ala Ala Lys Ala Ala Lys Tyr Gly Ala Ala Val Pro Gly Val Leu Gly Gly Leu Gly Ala Leu Gly Gly Val Gly Ile Pro Gly Gly Val Val Gly Ala Gly Pro Ala Ala Ala Ala Ala Ala Ala Lys Ala Ala Ala Lys Ala Ala Gln Phe Gly Leu Val Gly Ala Ala Gly Leu Gly Gly Leu Gly Val Gly Gly Leu Gly Val Pro Gly Val Gly Gly Leu Gly Gly Ile Pro Pro Ala Ala Ala Ala Lys Ala Ala Lys Tyr Gly Ala Ala Gly Leu Gly Gly Val Leu Gly Gly Ala Gly Gln Phe Pro Leu Gly Gly Val Ala Ala Arg Pro Gly Phe Gly Leu Ser Pro Ile Phe Pro Gly Gly Ala Cys Leu Gly Lys Ala Cys Gly Arg Lys Arg Lys
```

REFERENCES

1. Giannoudis, P. V., H. Dinopoulos, and E. Tsiridis, Bone substitutes: An update. Injury, 2005. 36(3, Supplement): p. S20-S27.
2. Panagiotis, M., Classification of non-union. Injury, 2005. 36(4, Supplement): p. S30-S37;
3. Zeckley, C., et al., The Aseptic Femoral and Tibial Shaft Non-Union in Healthy Patients—An Analysis of the Health-Related Quality of Life and the Socioeconomic Outcome. The Open Orthopaedics Journal, 2011. 5: p. 193-7;
4. Schindeler, A., et al., Bone remodeling during fracture repair: The cellular picture. Seminars in Cell & Developmental Biology, 2008. 19(5): p. 459-466;
5. Pape, H., A. Evans, and P. Kobbe, Autologous bone graft: properties and techniques. Journal of orthopaedic trauma, 2010. 24(Suppl 1): p. S36-40;
6. Lavini, F., C. Dall'Oca, and P. Bartolozzi, Bone transport and compression-distraction in the treatment of bone loss of the lower limbs. Injury, 2010. 41(11): p. 1191-1195;
7. Bobroff, G., S. Gold, and D. Zinar, Ten year experience with use of Ilizarov bone transport for tibial defects. Bulletin (Hospital for Joint Diseases (New York, N.Y.)), 2003. 61(3-4): p.101-7;
8. Maniatis, T. et al., Molecular Cloning: a laboratory manual, Second Edition, Cold Spring Harbor Laboratory Press;
9. Wu et al., (1999) Journal of Biological Chemistry, 274: 21719-21724;
10. Smith & Waterman. J. Mol. Biol. 147:195-197, 1981; Pearson, Genomics 11:635-650, 1991;
11. Altschul et al., Nucl. Acids Res. 25:3389-3402, 1997;

---

The invention claimed is:

1. A method of inducing formation of bone in an individual consisting essentially of the steps of
providing an individual having a bone fracture or void requiring bone formation, and
providing a therapeutically effective amount of uncrosslinked tropoelastin to the individual to induce the formation of bone in the individual,
thereby inducing bone formation in the individual, wherein the tropoelastin is administered by injection.

2. The method of claim 1, wherein the defect is a fracture and the individual is provided with the tropoelastin to promote the repair of the fracture.

3. The method of claim 2, wherein the tropoelastin is administered directly to bone at the site of the fracture.

4. The method of claim 1 wherein the tropoelastin is administered directly to the bone callus.

5. The method of claim 4 wherein the tropoelastin is administered in the form of a gel, putty or paste.

6. The method of claim 5 wherein the tropoelastin is administered to a periosteal surface.

7. The method of claim 1, wherein the defect is a void.

8. The method of claim 7 wherein the tropoelastin is administered directly to the bone at the site of the bone void.

9. The method of claim 8 wherein the tropoelastin is administered directly to the bone callus.

10. The method of claim 9 wherein the tropoelastin is administered by injection.

11. The method of claim 10 wherein the tropoelastin is administered in the form of a gel, putty or paste.

12. The method of claim 11 wherein the tropoelastin is administered to a periosteal surface.

13. The method of claim 1, wherein the tropoelastin is a SHELδ26A, as shown in SEQ ID NO: 1.

* * * * *

SEQUENCE LISTING

```
<160> NUMBER OF SEQ ID NOS: 1

<210> SEQ ID NO 1
<211> LENGTH: 698
<212> TYPE: PRT
<213> ORGANISM: Homo sapiens

<400> SEQUENCE: 1

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
                20                  25                  30

Gly Gly Lys Pro Leu Lys Pro Val Pro Gly Gly Leu Ala Gly Ala Gly
            35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
                100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
                180                 185                 190

Leu Pro Tyr Thr Thr Gly Lys Leu Pro Tyr Gly Tyr Gly Pro Gly Gly
            195                 200                 205

Val Ala Gly Ala Ala Gly Lys Ala Gly Tyr Pro Thr Gly Thr Gly Val
            210                 215                 220

Gly Pro Gln Ala Ala Ala Ala Ala Lys Ala Ala Lys Phe
225                 230                 235                 240

Gly Ala Gly Ala Ala Gly Val Leu Pro Gly Val Gly Gly Ala Gly Val
                245                 250                 255
```

```
Pro Gly Val Pro Gly Ala Ile Pro Gly Ile Gly Ile Ala Gly Val
            260                 265                 270
Gly Thr Pro Ala Ala Ala Ala Ala Ala Ala Ala Lys Ala Ala
        275                 280                 285
Lys Tyr Gly Ala Ala Gly Leu Val Pro Gly Pro Gly Phe Gly
    290                 295                 300
Pro Gly Val Val Gly Val Pro Gly Ala Gly Val Pro Gly Val Gly Val
305                 310                 315                 320
Pro Gly Ala Gly Ile Pro Val Val Pro Gly Ala Gly Ile Pro Gly Ala
                325                 330                 335
Ala Val Pro Gly Val Val Ser Pro Glu Ala Ala Lys Ala Ala
        340                 345                 350
Lys Ala Ala Lys Tyr Gly Ala Arg Pro Gly Val Gly Val Gly Gly Ile
        355                 360                 365
Pro Thr Tyr Gly Val Gly Ala Gly Phe Pro Gly Phe Gly Val Gly
    370                 375                 380
Val Gly Gly Ile Pro Gly Val Ala Gly Val Pro Ser Val Gly Gly Val
385                 390                 395                 400
Pro Gly Val Gly Gly Val Pro Gly Val Gly Ile Ser Pro Glu Ala Gln
                405                 410                 415
Ala Ala Ala Ala Ala Lys Ala Ala Lys Tyr Gly Val Gly Thr Pro Ala
                420                 425                 430
Ala Ala Ala Lys Ala Ala Lys Ala Ala Gln Phe Gly Leu Val
        435                 440                 445
Pro Gly Val Gly Val Ala Pro Gly Val Gly Val Ala Pro Gly Val Gly
    450                 455                 460
Val Ala Pro Gly Val Gly Leu Ala Pro Gly Val Gly Val Ala Pro Gly
465                 470                 475                 480
Val Gly Val Ala Pro Gly Val Gly Val Ala Pro Gly Ile Gly Pro Gly
                485                 490                 495
Gly Val Ala Ala Ala Lys Ser Ala Ala Lys Val Ala Ala Lys Ala
            500                 505                 510
Gln Leu Arg Ala Ala Ala Gly Leu Gly Ala Gly Ile Pro Gly Leu Gly
        515                 520                 525
Val Gly Val Gly Val Pro Gly Leu Gly Val Gly Ala Gly Val Pro Gly
    530                 535                 540
Leu Gly Val Gly Ala Gly Val Pro Gly Phe Gly Ala Val Pro Gly Ala
545                 550                 555                 560
Leu Ala Ala Ala Lys Ala Ala Lys Tyr Gly Ala Ala Val Pro Gly Val
                565                 570                 575
Leu Gly Gly Leu Gly Ala Leu Gly Gly Val Gly Ile Pro Gly Gly Val
        580                 585                 590
Val Gly Ala Gly Pro Ala Ala Ala Ala Ala Ala Lys Ala Ala Ala
    595                 600                 605
Lys Ala Ala Gln Phe Gly Leu Val Gly Ala Ala Gly Leu Gly Gly Leu
        610                 615                 620
Gly Val Gly Gly Leu Gly Val Pro Gly Val Gly Gly Leu Gly Gly Ile
625                 630                 635                 640
Pro Pro Ala Ala Ala Ala Lys Ala Ala Lys Tyr Gly Ala Ala Gly Leu
                645                 650                 655
Gly Gly Val Leu Gly Gly Ala Gly Gln Phe Pro Leu Gly Gly Val Ala
            660                 665                 670
```

-continued

```
Ala Arg Pro Gly Phe Gly Leu Ser Pro Ile Phe Pro Gly Gly Ala Cys
        675                 680                 685
Leu Gly Lys Ala Cys Gly Arg Lys Arg Lys
        690                 695
```